United States Patent [19]

Kuroda et al.

[11] Patent Number: 4,985,153

[45] Date of Patent: Jan. 15, 1991

[54] METHOD FOR SEPARATING BLOOD INTO BLOOD COMPONENTS, AND BLOOD COMPONENTS SEPARATOR UNIT

[75] Inventors: Toru Kuroda; Takao Nishimura, both of Oita, Japan

[73] Assignee: Asahi Medical Co., Ltd., Tokyo, Japan

[21] Appl. No.: 370,750

[22] Filed: Jun. 23, 1989

[30] Foreign Application Priority Data

Jun. 23, 1988 [JP] Japan ................... 63-153464
Jun. 23, 1988 [JP] Japan ................... 63-153465

[51] Int. Cl.$^5$ ..................... B01D 21/26; B01D 36/00
[52] U.S. Cl. ..................... 210/782; 210/206; 210/496; 210/767; 210/789; 210/806; 494/37; 604/406; 604/410
[58] Field of Search ............... 210/767, 782, 787, 789, 210/806, 206, 496; 494/37; 604/406, 408, 410

[56] References Cited

U.S. PATENT DOCUMENTS

| | | | |
|---|---|---|---|
| 3,870,042 | 3/1975 | Viguier | 604/406 |
| 4,330,410 | 5/1982 | Takenaka et al. | 210/767 |
| 4,512,763 | 4/1985 | Schneider | 604/5 |
| 4,596,657 | 6/1986 | Wisdom | 210/257.1 |
| 4,701,267 | 10/1987 | Watanabe et al. | 210/806 |
| 4,767,541 | 8/1988 | Wisdom | 210/787 |
| 4,810,378 | 3/1989 | Carmen et al. | 210/206 |

FOREIGN PATENT DOCUMENTS

| | | |
|---|---|---|
| 0155003 | 9/1985 | European Pat. Off. |
| 0266683 | 5/1988 | European Pat. Off. |
| 0267286 | 5/1988 | European Pat. Off. |
| 55-129755 | 10/1980 | Japan |
| WO84/00892 | 3/1984 | PCT Int'l Appl. |
| 1516698 | 7/1978 | United Kingdom |

OTHER PUBLICATIONS

"Advanced Methods for Leukocyte Removal by Blood Filtration", Abstract from Int'l. Workshop on the Role of Leucocyte Depletion in Blood Transfusion Practice, by T. Nishimura et al., Jul. 9, 1988, pp. 18–19.

"Use of Sterile Connecting Device to Prepare Leucocyte-Poor Filtered Red Cells in a Closed System", Abstract from Int'l. Workshop on the Role of Leucocyte Depletion in Blood Transfusion Practice, by J. James et al., Jul. 9, 1988, pp. 24–25.

"35 Days Storage of Leucocyte Free Red Blood Cells Concentrates: In Vitro Study", Abstract from Int'l. Workshop on the Role of Leucocyte Depletion in Blood Transfusion Practice, by M. Angue et al., Jul. 9, 1989, p. 46.

Primary Examiner—W. Gary Jones

[57] ABSTRACT

A method for separating blood into blood components aseptically in a closed system first filters whole blood through a filter for removing leukocytes or removing leukocytes and platelets, to produce filtered blood, which is passed to and collected in a primary bag fluid-tightly connected to the filter through a sealable, cuttable conduit, and the conduit is sealed and cut to disconnect the primary bag from the filter. The disconnected primary bag is subjected to centrifugation to separate the filtered blood into blood components. The method is useful for separately collecting leukocyte-removed blood components, particularly leukocyte-removed erythrocytes, leukocyte-removed plasma, leukocyte-removed platelets, etc., from the whole blood of a healthy human. A blood components separation unit which can advantageously be used in the practice of the above method is also disclosed.

24 Claims, 2 Drawing Sheets

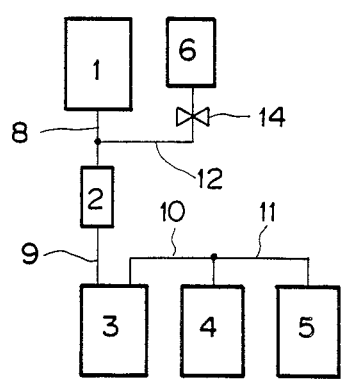
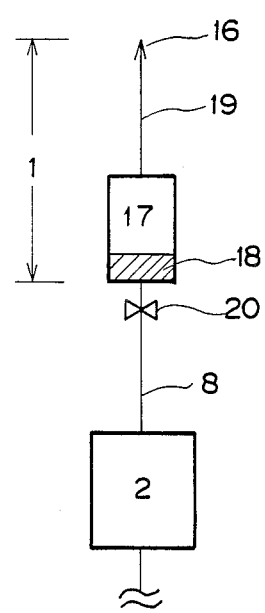
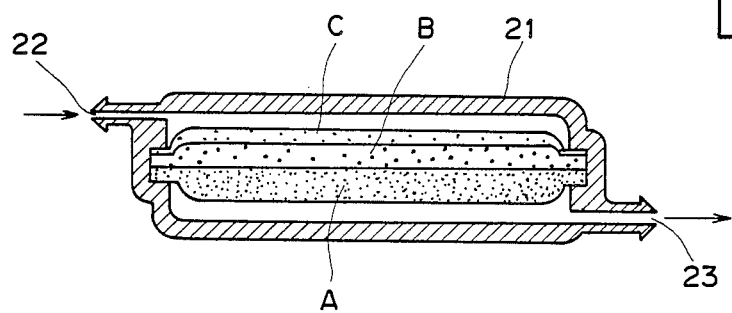
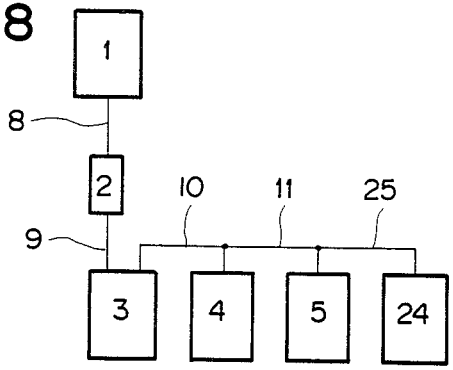

METHOD FOR SEPARATING BLOOD INTO BLOOD COMPONENTS, AND BLOOD COMPONENTS SEPARATOR UNIT

BACKGROUND OF THE INVENTION

1. Field of the Invention

The present invention relates to a method for separating blood into blood components aseptically in a closed system, which is useful for separately collecting leukocyte-removed blood components, particularly leukocyte-removed erythrocytes leukocyte-removed plasma, leukocyte-removed platelets, etc., from the whole blood of a healthy human. The present invention is also concerned with a blood components separator unit, which can advantageously be used in practice of the above-mentioned method.

2. Discussion of Related Art

In recent years, with the progress in medical science, particularly in immunology, there has been an increase in demand for transfusions of blood components. The blood component to be transfused is suitably chosen according to the purpose of therapy. In practicing the transfusions of blood components, leukocytes must be removed from the blood components for the following reason. The number of types of leukocytes is very large, differing from that of erythrocytes which, for example, is only 4 types, namely types A, B, O and AB under the ABO blood grouping system. Therefore, it is extremely difficult to match the blood type of leukocyte present in a blood component to be used for transfusion to the blood type of leukocyte of a patient who will be subjected to blood transfusion Therefore, when blood components from others are transfused into a patient without removing leukocytes therefrom, an antibody against the surface antigen present in the transfused leukocyte is produced in the body of the patient since such leukocytes contained therein, in most cases, are foreign substances to the body of a patient. The repeated transfusion of blood containing such foreign leukocytes causes the antigen-antibody reaction to occur between the produced anti-leukocyte antibody and the surface antigen of the transfused leukocytes, so that an adverse effect, such as fever and headache, is caused. In recent years, various filter means have been developed for removing leukocytes from blood components to be used for transfusions. Such filter means can remove leukocytes efficiently from whole blood or various blood components. Therefore, by the use of the filter means for removing leukocytes, the above-mentioned adverse effect can be suppressed.

Generally, in practicing the removal of leukocytes from whole blood or blood components by means of filter means, the filtering means is connected to a bag containing whole blood or blood components. However, it is difficult to connect the filter means aseptically to the bag unless a specific apparatus is used. Therefore, conventionally, in the removal of leukocytes, the leukocyte-removed blood or the leukocyte-removed blood components would be likely to be contaminated with various germs. Accordingly, it has been obligatory to use the leukocyte-removed blood or blood components within 24 hours after the preparation thereof. Therefore, it is earnestly desired in the art to develop an aseptic system for removing leukocytes from whole blood or blood components.

In U.S. Pat. No. 4,596,657, one aseptic system for removing leukocytes is disclosed. Illustratively stated, a multiple-blood bag system comprising a primary bag, at least two satellite bags connected to the primary bag through conduit means, and a filter means for removing leukocytes integrally disposed between the primary bag and one of the satellite bags is disclosed. The bag system is used in the following manner. Blood is collected in the primary bag and subjected to centrifugation so as to be separated into a plasma layer and an erythrocyte concentrate layer. The separated plasma layer is then transferred from the primary bag into a first satellite bag through conduit means which is fluid-tightly disposed between the primary bag and the first satellite bag. The erythrocyte concentrate layer is caused to pass through the filter means to remove by filtration leukocytes from the erythrocyte concentrate and the resultant leukocyte-removed erythrocyte concentrate is collected in the second satellite bag which is connected to the primary bag through the filter means. With this bag system, leukocytes present in the erythrocyte concentrate are removed, but leukocytes present in the separated plasma disadvantageously cannot be removed. Further, this bag system has the following disadvantages. That is, when the blood collected in the primary bag is separated by centrifugation, the filter means must be placed in a centrifuge together with the primary bag and the satellite bags, leading to a danger that the filter means and the bags are likely to be destroyed due to the centrifugal force and the friction between the bags and the filter means during the centrifugation Therefore, this bag system have not been widely used.

European Patent Application Publication No. 0 266 683 A2 discloses another bag system as a blood components collector unit This unit comprises a cannula, a blood collection bag, a filter means for removing leukocytes and a filter membrane type blood components separator which are connected through tubes. The unit also comprises a plasma collection reservoir and a blood cell collection reservoir, both of which are connected to the blood components separator through tubes, wherein each connection through each tube is in a fixed fashion, thereby providing a unified connection. By the use of this unit, whole blood collected from a donor can be separated into leukocyte-removed plasma and leukocyte-removed blood cell-enriched blood by filtration, using a combination of the filter means and the membrane type blood components separator. However, this unit has disadvantages in that the plasma collection ratio, i.e., the ratio of the amount of the filtration-separated plasma to the amount of the collected whole blood is small as compared to the plasma collection ratio obtained by centrifugal separation; that proteins having relatively high molecular weight which are present in plasma are likely to be prevented from passing through the filter membrane of the separator so that the recovery of such proteins in the separated plasma is low; that by the contact of whole blood with the membrane, complement components in the blood are unfavorably activated, causing the quality of the blood to be lowered; and that the membrane type blood components separator is expensive.

SUMMARY OF THE INVENTION

The present inventors have made extensive and intensive studies with a view toward developing a method and a unit for separating blood into blood components aseptically, which are free from the above-mentioned drawbacks. As a result, it has been found that when whole blood is first filtered by filter means for removing leukocytes to collect the leukocyte-removed blood in a primary bag and the primary bag is then aseptically disconnected from the filter means and subjected to centrifugation. Blood components, such as plasma, erythrocytes and platelets in leukocytes-free form can be aseptically and readily obtained without the danger of damage to the filter means and the primary bag. Based on the above-mentioned finding, the present invention has been completed.

Accordingly, it is an object of the present invention to provide a method for aseptically separating blood into at least two blood components, for example, leukocyte-removed erythrocyte, leukocyte-removed plasma, leukocyte-removed platelets and the like, without the danger of damage to the filter means and the bag.

It is another object of the present invention to provide a novel blood components separator unit which is advantageously used in the above-mentioned method for separating blood into blood components.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein:

FIG. 5 is a diagrammatic view of still a further form of the blood components separator unit of the present invention comprising blood collector means 1, filter means 2 for removing leukocytes, primary bag 3, two satellite bags 4 and 5 and physiologically isotonic solution-containing bag 6;

FIG. 6 is a diagrammatic view illustrating one form of the blood collector means 1 to be used in the blood separator unit of the present invention, which comprises cannula 16 and blood collection bag 17, shown together with filter means 2;

FIG. 7 is a diagrammatic cross-sectional view of filter means 2 used in Example 1; and FIG. 8 is a diagrammatic view of still a further form of the blood components separator unit of the present invention comprising blood collector means 1, filter means 2 for removing leukocytes, primary bag 3 and three satellite bags 4, 5 and 24.

In FIGS. 1 through 8, like parts or portions are designated by like numerals.

DETAILED DESCRIPTION OF THE INVENTION

According to the present invention, a method for separating blood into blood components is provided, which comprises the steps of:

(a) providing blood collector means fluid-tightly connected to filter means for removing leukocytes or removing leukocytes and platelets from whole blood, said filter means being fluid-tightly connected to a primary bag through sealable, cuttable conduit means;

(b) collecting, from a donor, whole blood comprising plasma, erythrocytes, leukocytes and platelets;

(c) passing the whole blood through said filter means to produce a filtered blood containing the plasma, the erythrocytes and the platelets or containing the plasma and the erythrocytes;

(d) discharging the filtered blood from said filter means into said primary bag through said conduit means;

(e) sealing said conduit means at least at one portion intermediate ends thereof;

(f) cutting said conduit means to separate said conduit means into a filter means-side unsealed or sealed conduit portion and a primary bag-side sealed conduit portion to thereby disconnect from said filter means said primary bag containing the filtered blood, said disconnected primary bag being sealed by virtue of said primary bag-side sealed conduit portion connected to said primary bag; and (g) centrifuging the filtered blood in said primary bag.

Figure 1:
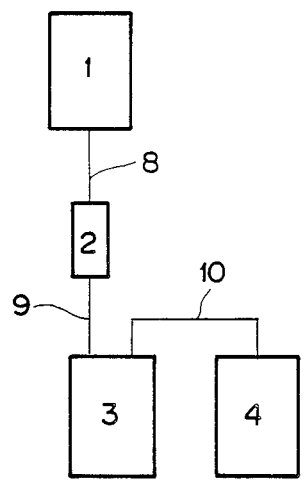
FIG. 1 is a diagrammatic view of one form of the blood components separator unit of the present invention comprising blood collector means 1, filter means 2 for removing leukocytes or removing leukocytes and platelets, primary bag 3 and satellite bag 4.

Referring now to FIG. 1, the method of the present invention will be explained below.

In step (a), blood collector means 1 is provided. Blood collector means 1 is fluid-tightly connected to filter means 2 for removing leukocytes or removing leukocytes and platelets, which filter means 2 in turn is fluid-tightly connected to primary bag 3 through sealable, cuttable conduit means 9. The blood collector means generally has a cannula. In one embodiment, the blood collector means comprises cannula 16 and blood collection bag 17 containing anticoagulant 18 as shown in FIG. 6. The whole blood collected contacts the anticoagulant in the blood collection bag, thereby preventing the coagulation of whole blood. In this embodiment, the blood collection bag 17 is fluid-tightly connected to cannula 16.

Examples of suitable anticoagulants include compositions, such as an "ACD" solution and a "CPD" solution. The ACD solution comprises glucose, trisodium citrate and citric acid. The composition of the ACD solution varies according to country. In Japan, an ACD solution is generally employed containing 22.0 g trisodium citrate, 8.0 g citric acid and 22.0 g of glucose per 1000 ml. The CPD solution generally contains 26.30 g of trisodium citrate, 3.27 g of citric acid, 23.20 g of glucose and 2.51 g of sodium dihydrogen phosphate per 1000 ml.

The anticoagulant is placed in the blood collection bag in an amount sufficient for preventing the quantity of whole blood, which is intended to collect in the blood collection bag, from coagulating. The amount of the anticoagulant varies not only according to the quantity of whole blood which is intended to be collected but also according to the type and composition of the anticoagulant. For example, in the case of an ACD solution adopted in Japan, the amount of the anticoagulant may generally be 15 ml per 100 ml of whole blood. In the case of a CPD solution adopted in Japan, the amount of the anticoagulant may be 14 ml per 100 ml.

In step (b), whole blood comprising plasma, erythrocytes, leukocytes and platelets is collected from a donor by blood collector means. Particularly, the vein of a donor is punctured by means of the cannula and whole blood is collected from the vein through the cannula. The blood collection operation may be conducted utilizing gravity. The blood collection operation may also be conducted using pumping means, etc.

In order to remove leukocytes or remove leukocytes and platelets from whole blood stably without causing blood coagulation, it is preferred that an anticoagulant is added to the whole blood before passing the whole blood through the filter means. The addition of an anticoagulant to whole blood may be conducted by passing an anticoagulant from an anticoagulant-containing bag into conduit means 8 which connects blood collector means 1 with filter means 2. This method is advantageous in that the blood collection operation, the mixing operation of blood with an anticoagulant and the blood filtration operation by the filter means can be continuously conducted. In this method, in order to ensure the mixing of the whole blood with an anticoagulant, mixing means, such as a drip chamber, may be aseptically inserted in conduit means 8. On the other hand, when blood collector means 1 comprises blood collection bag 17 containing an anticoagulant 18 as mentioned above, the whole blood collected through cannula 16 is mixed with the anticoagulant in blood collection bag 17. This method is most preferred from the standpoint of secure mixing of the whole blood with an anticoagulant.

When a filtration medium having excellent compatibility with blood is used for filter means 2, the collected blood need not be mixed with an anticoagulant before being subjected to filtration. This is advantageous in that blood collection means 1 may have only a cannula so that the blood component collector unit becomes simple In this case, primary bag 3 may contain an anticoagulant to prevent the coagulation of the filtered blood.

In step (c), the collected whole blood is passed through filter means 2 to produce a filtered blood. The filter means may suitably be chosen from two types of filter means, that is, filter means for removing leukocytes and filter means for removing leukocytes and platelets according to the types of blood components which are intended to be obtained by filtration in this step. When filter means for removing leukocytes is used, the filtered blood contains the plasma, the erythrocytes and the platelets, substantially free from leukocytes. When filter means for removing leukocytes and platelets is used, the filtered blood contains the plasma and the erythrocytes, substantially free from leukocytes and platelets.

Examples of filtration media for use in the filter means include a fibrous medium, a porous medium and a particulate medium Of these, a fibrous medium is most preferred from the standpoint of leukocyte removal efficiency. The fibrous medium may be in any form, that is, it may be in the form of a woven fabric or a non-woven fabric, or in an entangled mass form. Of these, the most preferred is a non-woven fabric from the standpoint of blood permeability through the medium. The diameter of the fibrous medium for use in the filter means is generally in the range from about 0.3 $\mu$m to about 20 $\mu$m. From the viewpoint of leukocyte removal efficiency, it is preferred that the diameter be in the range from about 0.3 to about 10 $\mu$m. More preferably, the diameter is in the range from about 0.3 to about 3 $\mu$m.

Examples of fibrous media for use in the filter means include synthetic fibers such as polyester fibers, for example, polyethylene terephthalate fiber and polybutylene terephthalate fiber, polyamide fibers, polyacrylonitrile fibers, polymethylmethacrylate fibers, polyethylene fibers and polypropylene fibers; semi-synthetic fibers such as cellulose acetate fibers; regenerated fibers such as cuprammonium rayon fibers, viscose rayon fibers, and viscose staple fibers; natural fibers such as cotton fibers, silk and wool; inorganic fibers such as glass fibers and carbon fibers. Of these, synthetic fibers are preferably employed from the standpoint of ease in controlling the diameter of the fiber, ease in producing on a commercial scale and the like.

When it is intended to remove leukocytes and platelets by the filter means, it is preferred that the filter means be comprised of the above-mentioned filtration medium, the surface of which has been rendered hydrophobic, or comprised of the above-mentioned filtration medium and positive charges bonded to the surface thereof. The above-mentioned filtration medium can be rendered hydrophobic by a customary method, for example, by coating a hydrophobic polymer on the surface of the filtration medium or by graft-polymerizing a hydrophobic monomer. On the other hand, bonding of positive charges to the surface of the above-mentioned filtration medium can be accomplished by a method in which a polymer having a nitrogen-containing basic functional group is coated on the surface. Examples of nitrogen-containing basic functional groups include a primary amino group, a secondary amino group, a tertiary amino group, and a quaternary ammonium group, and also include nitrogen-containing aromatic ring groups such as a pyridyl group and an imidazolyl group. The polymer having a nitrogen-containing basic functional group may be prepared from at least one monomer having a nitrogen-containing basic functional group by a customary polymerization method. Examples of monomers containing nitrogen-containing basic functional groups include allyl-amine; (meth)acrylic acid derivatives such as dimethylaminoethyl (meth)acrylate, diethylaminoethyl (meth)acrylate, dimethylaminopropyl (meth)acrylate, 3-dimethylamino-2-hydroxypropyl (meth)acrylate; styrene derivatives such as p-dimethylaminomethylstyrene, p-diethylaminoethylstyrene; vinyl derivatives of nitrogen-containing aromatic compounds such as 2-vinylpyridine, 4-vinylpyridine, 4-vinylimidazole; and derivatives thereof, such as obtained by converting the above-mentioned vinyl compounds to a quaternary ammonium salt using a halogenated alkyl or the like. Of these monomers, dimethylaminoethyl (meth)acrylate and diethylaminomethyl (meth)acrylate are preferably employed from the viewpoints of availability, ease in handling in the polymerization, and blood filtration performance of the resulting surface portion of the filtration medium.

Further, the bonding of positive charges to the surface of the filtration medium can also be accomplished by a method in which a monomer of the type mentioned above having a nitrogen-containing basic functional group is graft-polymerized onto the surface of the filtration medium in a manner as described in, for example, "Surface Modification of Polymer", Fumio Ide, 1987, published by Kindai Henshu Ltd., Japan. Still further, such bonding can be accomplished by a method in which the surface is treated with a chemical The above-mentioned methods for bonding positive charges to the surface of the filtration medium are described in, for example, European Patent Application Publication No. 0267286.

When it is not intended to remove platelets, but intended to remove only leukocytes in step (c), it is preferred that an anti-thrombotic material be coated on the surface of the above-mentioned filtration medium in order to improve platelet passage therethrough. Examples of anti-thrombotic materials include a polyether urethane, a polyhydroxyethyl methacrylate, a silicone, a collodion, a heparinized hydrophilic polymer, a urokinase-immobilized material, a Flurbiprofen-Beuzalkonium complex and the like. The coating method is described in, for example, Japanese Patent Application Laid-Open Specification No. 55-129755. Moreover, from the viewpoint of attaining excellent platelet passage and leukocyte removal, it is preferred that both a hydrophilic group and a nitrogen-containing basic functional group be bonded to the surface of the filtration medium. The bonding of a hydrophilic group and a nitrogen-containing basic functional group to the surface of the filtration medium may be conducted substantially according to the method described in European Patent Application Publication No. 0267286. Examples of hydrophilic groups include hydroxyl groups and amido groups. Examples of nitrogen-containing basic functional groups are the same as mentioned above. In this case, it is requisite that the portion which contains hydrophilic groups and nitrogen-containing basic functional groups have a basic nitrogen atom content of from 0.2 to 4.0% by weight. The term "basic nitrogen atom" used herein means a nitrogen atom in the above-mentioned nitrogen-containing basic functional groups. If the basic nitrogen atom content is less than 0.2% by weight, the filtration medium becomes less adhesive not only to platelets but also to leukocytes, thereby rendering it impossible to selectively remove leukocytes On the other hand, if the basic nitrogen atom content is more than 4.0% by weight, the filtration medium becomes adhesive not only to leukocytes but also to platelets, thus rendering it impossible for leukocytes to be selectively removed The more preferable range of the basic nitrogen atom content is from 0.3 to 1.5% by weight. With respect to the most suitable contents of the basic nitrogen atoms in various raw materials for the filtration medium of the present invention, they vary according to the types of the functional groups contained in these raw materials and the conditions under which the filtration medium would be used (e.g. they vary a lot depending on the type of an anticoagulant to be added to the blood).

In the present invention, molar amount of the ionic hydrophilic group may preferably be at least equal to, more preferably at least three times as large as the molar amount of the basic nitrogen atom.

The amounts of the nitrogen-containing basic functional groups and the ionic hydrophilic groups, and the basic nitrogen atom content can be measured by known methods such as an infrared absorptiometric method using a multiple total reflection infrared spectrometer, and elementary analysis.

The capacity of the filtration medium of the filter means for blood introduced thereinto is not specifically limited When the capacity of the filter medium for blood is too large, a large volume of blood is left in the filtration medium so that the volume of filtered blood is decreased, leading to a lowering of the yield of the ultimately obtained blood components. Therefore, the capacity of the filter medium for blood is generally adjusted to 40% or less, preferably 20% or less, and more preferably 10% or less by volume, based on the volume of the collected blood.

By passing whole blood through the filter means, filtered blood is produced. When filter means for removing leukocytes is used, a filter blood is produced containing the plasma, the erythrocytes and the platelets, substantially free from leukocytes. When filter means for removing leukocytes and platelets is used, a filtered blood is produced containing the plasma and the erythrocytes, substantially free from leukocytes and platelets.

In order to complete the filtration of the whole blood, it is preferred that following step (d) and prior to step (e), a physiologically isotonic solution be passed through the filter means. As a physiologically isotonic solution, any conventional solutions may be used which avoid damage to the blood components and do not adversely affect a living body. Examples of physiologically isotonic solutions include a physiological saline, a physiological salt solution such as Ringer's solution, and the like. In this connection, however, it should be noted that passing the physiologically isotonic solution through the filtration medium is, on one hand, preferred from the viewpoints of filtration of all of the collected whole blood as described above, but, on the other hand, it has a drawback in that the filtered blood is disadvantageously caused to be diluted with a physiologically isotonic solution. In order to decrease such dilution, the amount of a physiologically isotonic solution passing through the filtration medium should be reduced. In view of the above, it is preferred that the volume of the physiologically isotonic solution be in the range of from 50% to 150%, based on the capacity of the filtration medium for blood.

Figure 3:
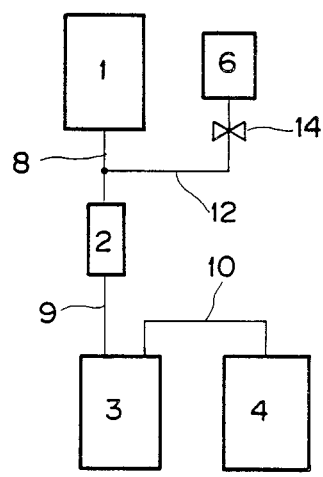
FIG. 3 is a diagrammatic view of still another form of the blood components separator unit of the present invention comprising blood collector means 1, filter means 2 for removing leukocytes or removing leukocytes and platelets, primary bag 3, satellite bag 4 and physiologically isotonic solution-containing bag 6.

As shown in FIGS. 3 and 5, the physiologically isotonic solution to be passed through the filter means may be contained in auxiliary bag 6 (hereinafter referred to as "physiologically isotonic solution-containing bag") which is fluid-tightly connected to filter means 2 through conduit means 12 branched from conduit means 8 so that the physiologically isotonic solution can be supplied aseptically to the filter means.

In step (d), the filtered blood is passed from filter means 2 into primary bag 3 through sealable, cuttable conduit means 9 (see FIG. 1).

In step (e), after the filtered blood is collected in primary bag 3, sealable, cuttable conduit means 9 is sealed at least at one portion intermediate the length thereof The sealing of the sealable, cuttable conduit means can be performed by press-sealing by means of, for example, a deformable metal (e.g. aluminum) ring or by heat-sealing by means of a heat sealer.

In step (f), sealable, cuttable conduit means 9 which has been sealed is cut to separate conduit means 9 into two sections or portions. That is, a filter means-side unsealed or sealed conduit portion and a primary bag-side sealed conduit portion are formed. The filter means 2 is thereby separated from primary bag 3 containing the filtered blood. The disconnected primary bag 3 is sealed by virtue of the primary bag-side sealed conduit portion connected to the primary bag.

In step (g), the filtered blood in primary bag 3 is subjected to centrifugation. Referring to FIG. 1, primary bag 3 containing the filtered blood, which is fluid-tightly connected to satellite bag 4 through conduit means 10, is placed in a centrifuge, followed by centrifugation. During the centrifugation, conduit means 10 connecting primary bag 3 and satellite bag 4 is pinched by a clip or the like to seal the conduit means temporarily so that the filtered blood in primary bag 3 may not be transferred into satellite bag 4.

When the whole blood is passed through the filter means for removing leukocytes and platelets, the filtered blood containing the erythrocytes and the plasma is produced. The filtered blood is separated into an erythrocytes layer consisting substantially of the erythrocytes and a plasma layer consisting substantially of the plasma by centrifugation. The centrifugation may be conducted under powerful conditions, that is, at $4,800 \times g$ (acceleration of gravity), at 4° to 6° C. for 3 to 4 minutes or at $3,000 \times g$, at 4° to 6° C. for 5 to 7 minutes. By the centrifugation, the filtered blood is separated into two layers, that is, an upper plasma layer and a lower erythrocytes layer.

After centrifugation, the plasma in the upper layer is transferred into satellite bag 4 which is fluid-tightly connected to primary bag 3 through sealable, cuttable conduit means 10. The transfer of the plasma into the satellite bag can be performed by externally applying pressure to the primary bag 3 using a conventionally used apparatus, such as a commercially available separation stand. Alternatively, the erythrocytes in the lower layer may be transferred into the satellite bag. In this case, conduit means 10 connecting primary bag 3 and satellite bag 4 is pinched by a clip or the like to seal the conduit means temporarily, and primary bag 3 and satellite bag 4 are then placed in a centrifuge so that the portion of primary bag 3 at which primary bag 3 is connected to satellite bag 4 through conduit means 10 is directed downward, followed by centrifugation. Then, satellite bag 4 is suspended below primary bag 3 and the clip is removed from conduit means 10 so that the lower erythrocytes layer in the primary bag flows into the satellite bag through conduit means 10 by the force of gravity.

After the transfer of the plasma or the erythrocytes into satellite bag 4, conduit means 10 disposed between primary bag 3 and satellite bag 4 is sealed at a portion intermediate the length thereof by means of a heat sealer or the like and cut at a position in the sealed portion to separate conduit means 10 into a primary bag-side sealed conduit portion and a satellite bag-side sealed conduit portion and to thereby disconnect primary bag 3 from satellite bag 4. The sealing of the conduit means connecting the primary bag and the satellite bag may alternatively be conducted at two portions intermediate the length thereof, followed by cutting the conduit means at a position between the two sealed portions. The thus disconnected primary bag aseptically contains one of the blood components, i.e., the erythrocytes or the plasma and the satellite bag aseptically contains the remainder of the blood components.

Figure 2:
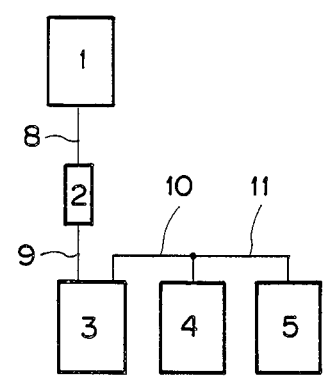
FIG. 2 is a diagrammatic view of another form of the blood components separator unit of the present invention comprising blood collector means 1, filter means 2 for removing leukocytes, primary bag 3 and two satellite bags 4 and 5.

When filter means for removing leukocytes is used to obtain a filtered blood containing the erythrocytes, the plasma and the platelets and the filtered blood is then subjected to centrifugation, the filtered blood may be separated, for example, into two fractions, namely, an erythrocytes layer consisting substantially of the erythrocytes and a mixture layer of the plasma and the platelets (hereinafter referred to as "platelet-rich plasma"), or a platelets-containing erythrocyte layer and a plasma layer consisting substantially of the plasma (platelet-poor plasma). In this case, one satellite bag needs to be connected to the primary bag through sealable, cuttable conduit means as shown in FIG. 1. When the erythrocytes and the platelet-rich plasma are intended to be obtained, the centrifugation is conducted under gentle conditions, that is, at $1,100 \times g$, at 4° to 6° C. for 5 to 6 minutes or at $300 \times g$, at 4° to 6° C. for 15 to 20 minutes. By the centrifugation, the filtered blood is separated into two layers, that is, an upper platelet-plasma layer and a lower erythrocytes layer After centrifugation, the platelet-rich plasma in the upper layer is transferred into satellite bag 4. On the other hand, when the platelet-containing erythrocytes and the platelet-poor plasma are intended to be obtained, the centrifugation is conducted under powerful conditions, that is, at $4,800 \times g$, at 4° to 6° C. for 3 to 4 minutes or at $3,000 \times g$, at 4° to 6° C. for 5 to 7 minutes. By the centrifugation, the filtered blood is separated into two layers, that is, an upper platelet-poor plasma layer and a lower platelet-containing erythrocytes layer. After centrifugation, the platelet-poor plasma as the upper layer is transferred into satellite bag 4. The filtered blood may alternatively be separated into three fractions, that is, an erythrocytes layer consisting substantially of the erythrocytes, a plasma layer consisting substantially of the plasma and a platelets layer consisting substantially of the platelets by centrifugation. In this case, at least two satellite bags need to be connected to the primary bag through sealable, cuttable conduit means as shown in FIG. 2. In FIG. 2, first satellite bag 4 and second satellite bag 5 are connected to primary bag 3 through conduit means 10 and 11, respectively. Conduit means 11 is branched from conduit means 10. The separation of the filtered blood by centrifugation into three blood component layers, namely, the erythrocytes layer, the plasma layer and the platelets layer, can be conducted in various manners.

For example, the filtered blood may be separated into three blood components in the following manner. First, the filtered blood is separated into two layers in the primary bag, namely a lower erythrocytes layer and an upper mixture layer of the plasma and the platelets. The upper mixture layer or the lower erythrocytes layer is transferred into one of the first and second satellite bags. Next, the transferred mixture is subjected to centrifugation to separate the mixture into a plasma layer and a platelets layer, one of which, namely, the plasma layer or the platelets layer, is transferred into the other satellite bag remaining empty. Before subjecting the mixture layer to centrifugation, the bag containing the erythrocytes layer may be disconnected from the two other bags, one of which contains the mixture layer of the plasma and the platelets and the other of which is empty, by sealing and cutting the conduit means in the same manner as mentioned above.

In the above method in which the filtered blood is separated into three layers, the centrifugation is conducted under powerful conditions, for example, at $4,800 \times g$, at 4° to 6° C. for 3 to 4 minutes or at $3,000 \times g$, at 4° to 6° C. for 5 to 7 minutes. In the above method in which the filtered blood is separated into two layers, the first centrifugation for separating the filtered blood into an erythrocytes layer consisting substantially of the erythrocytes and a mixture layer of the plasma and the platelets is conducted under gentle conditions, for example, at $1,100 \times g$, at 4° to 6° C. for 5 to 6 minutes or at $300 \times g$, at 4° to 6° C. for 15 to 20 minutes, and the second centrifugation for separating the mixture layer into a plasma layer consisting substantially of the plasma and a platelets layer consisting substantially of the platelets is conducted under powerful conditions, that is, at $4,800 \times g$, at 4° to 6° C. for 3 to 4 minutes or at $3,000 \times g$, at 4° to 6° C. for 5 to 7 minutes.

After the erythrocytes layer, the plasma layer and the platelets layer have been separately collected respectively in the primary bag and the first and second satellite bags, the three bags are disconnected from one another by sealing and cutting the conduit means connecting them in the same manner as mentioned above.

In a preferred mode of the method for separating whole blood into three blood component layers, namely the erythrocytes layer, the plasma layer and the platelets layer, the filtered blood is separated into an erythrocytes layer, a plasma layer and a platelets layer, and following step (g), two of the layers are individually separated from the remainder to obtain the separated erythrocytes layer, the separated plasma layer and the separated platelets layer so that the separated platelets layer contains a small amount of the plasma and a small amount of the erythrocYtes, but the separated erythrocytes layer and the separated plasma layer consist substantially of the erythrocytes and the plasma, respectively, and the separated platelets layer containing a small amount of the plasma and a small amount of the erythrocytes is separated into the erythrocytes and a platelet concentrate containing the platelets and the plasma. In practicing this mode, three satellite bags are employed. As shown in FIG. 8, primary bag 3 is fluid-tightly connected to first satellite bag 4 through conduit means 10, which in turn is fluid-tightly connected to second satellite bag 5 through conduit means 11, which in turn is fluid-tightly connected to third satellite bag 24 through conduit means 25. In this mode, the blood having passed through filter means 2 which is capable of removing leukocytes but allowing platelets to pass therethrough is collected in primary bag 3. Primary bag 3 is disconnected from filter means 2 in the manner as mentioned above.

Primary bag 3 and satellite bags 4, 5 and 24 are set in a centrifuge, followed by centrifugation under the powerful conditions. As a result, the blood contained in primary bag 3 is separated into a lower erythrocytes layer, an intermediate platelets layer and an upper plasma layer. Two of the three layers are separately transferred into first satellite bag 4 and second satellite bag 5. The transfer of the two layers is conducted in a manner such that the platelets layer contains a small amount of the plasma and a small amount of the erythrocytes, but each of the erythrocytes layer and the plasma layer does not contain the other blood components. The bag in which the erythrocytes are contained and the bag in which the plasma is contained are disconnected from the other bags. The disconnection is conducted by sealing and cutting conduit means in the same manner as mentioned above. The platelets, a small amount of the plasma and a small amount of the erythrocytes are mixed homogeneously by, for example, gently pressing the bag by hand. The resultant mixture in the bag is centrifuged at $1,170 \times g$, at 20° to 24° C. for 5 minutes to thereby separate the mixture into a platelet concentrate layer and an erythrocytes layer. Then, the platelet concentrate is transferred into the other bag (empty), leaving the erythrocytes. The bag containing the platelet concentrate is disconnected from the bag in which the erythrocytes are left, in the same manner as mentioned above.

According to this method, the platelets are obtained in the form of the platelet concentrate. This is advantageous in that the collected platelets are unlikely to suffer from damage. With respect to the blood components separation to be conducted subsequent to the disconnection of the filter means from the primary bag and the three satellite bags in the preferred mode mentioned above, reference may be made to, for example, Yuketsugakkaishi (Journal of Blood Transfusion, Japan, Vol. 32, p. 237 and p. 303, 1986.

Figure 4:
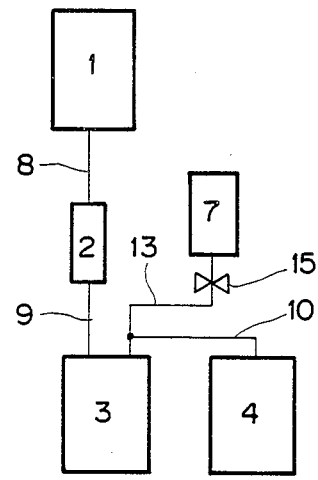
FIG. 4 is a diagrammatic view of a further form of the blood components separator unit of the present invention comprising blood collector means 1, filter means 2 for removing leukocytes or leukocytes and platelets, primary bag 3, satellite bag 4 and erythrocyte preservative-containing bag 7.

If desired, a preservative for erythrocytes may be added to the separated erythrocytes. Examples of reservatives for erythrocytes include a physiologically isotonic solution containing at least one erythrocyte preservative such as adenine, mannitol, sorbitol and guanosine. The amount of the preservative to be added to the erythrocytes is not specifically limited. Generally, the preservative is added in an amount of about 50 to 100 ml in terms of the volume per 400 to 500 ml of whole blood. As shown in FIG. 4, the preservative for erythrocytes may preferably be supplied from an erythrocyte preservative-containing bag 7 to an erythrocytes-containing bag through conduit means 13 fluid-tightly connecting the former to the latter. With respect to the preservative for erythrocytes, reference may be made to, for example, Transfusion, Vol. 27, pp. 178–182, 1987.

With respect to the operation to be conducted subsequent to the disconnection of the filter means from the primary bag and the satellite bag system, reference may be made to, for example, "The Standards of Operations in Red Cross Blood Center: Technical Division", 1985, published by the Enterprise Department, the Japanese Red Cross Society.

In another aspect of the present invention, a blood components separator unit is provided which is advantageously used in practicing the above-mentioned method for separating blood into blood components. That is, according to the present invention, a blood components separator unit is provided comprising:

means for collecting blood;

filter means for removing leukocytes or removing leukocytes and platelets, said filter means having a filtrate outlet;

first conduit means for connecting the means for collecting blood to the filter means;

a primary bag;

second conduit means for connecting the filtrate outlet of said filter means to said primary bag, said second conduit means being sealable and cuttable;

a satellite bag system; and additional conduit means for connecting the satellite bag system to said primary bag, the additional conduit means being sealable and cuttable, wherein connections of the first conduit means between the means for collecting blood and filter means, connections of the second conduit means between the filtrate outlet and primary bag and connections of the additional conduit means between the primary bag and satellite bag system are fixed, thereby providing unified connections.

Referring now to FIG. 1, a diagrammatic view is shown of one form of a blood components separator unit of the present invention which is useful for obtaining the plasma layer and the erythrocytes layer as blood components. Blood collector means 1 is connected to filter means 2 for removing both leukocytes and platelets through first conduit means 8. Blood collector means 1 may be a cannula only. Alternatively, as shown in FIG. 6, blood collector means 1 may comprise cannula 16 and blood collection bag 17 which is connected to cannula 16 through fifth conduit means 19. As the cannula 16, a hollow needle which is customarily used for collecting blood from a vein is generally employed. As is shown in FIG. 6, blood collection bag 17 may contain anticoagulant 18 to prevent coagulation of whole blood which is collected in the blood collection bag 17 from a vein of a donor through the cannula 16 and conduit means 19. Examples of suitable anticoagulants and the amount of the anticoagulant to be used are as described above. In FIG. 6, filter means 2 is connected to blood collection bag 17 on its side remote from cannula 1. However, a portion of blood collection bag 17 to which filter means 2 is to be connected through first conduit means 8 is not critical and filter means 2 may be connected to blood collection bag 17 at any portion thereof other than the portion to which cannula 16 is connected, as long as filter means 2 is so designed as to conform to the intended connection.

When blood collector means 1 comprises cannula 1 and blood collection bag 17 containing anticoagulant 18, first valve means 20 is provided in conduit means 8 so that a predetermined quantity of whole blood may be collected and temporarily pooled in bag 17 before whole blood is passed into filter means 2. The valve means is designed to be aseptically operable by manual manipulation from outside of the first conduit means. Various types of valve means which are aseptically operable have been proposed in the art. Examples of valve means are described in, for example, European Patent Application Publication No. 0266683, U.S. Pat. No. 4,294,247 and the like.

Filter means 2 has a filtrate outlet from which filtered blood is discharged. The filter means may suitably be chosen from two types of filter means, that is, filter means for removing leukocytes or filter means for removing both leukocytes and platelets according to the type of blood components which are intended to be obtained by filtration. When filter means for removing leukocytes is used, the filtered blood contains the plasma, the erythrocytes and the platelets. When filter means for removing leukocytes and platelets is used, the filtered blood contains the plasma and the erythrocytes. Examples of filtration media for use in the filter means are as described above.

Primary bag 3 is connected to the filtrate outlet of filter means 2 through second conduit means 9. Second conduit means 9 is sealable and cuttable. The sealing of second conduit means 9 may be conducted, for example, by heat-sealing by means of a heat sealer or by press-sealing by means of, for example, a deformable metal (e.g. aluminum) ring. The material of second conduit means 9 is not critical and any material used for tubes of a conventional blood collection apparatus may be used as long as the second conduit means is sealable and cuttable. Generally, polyvinyl chloride is used as a material for the second conduit means.

A satellite bag system is connected to the primary bag through conduit means. When filter means for removing leukocytes and platelets is used so that two blood component layers, namely the erythrocytes layer and the plasma layer may be obtained, one satellite bag 4 is connected to primary bag 3 through third conduit means 10 (see FIG. 1). However, it is noted that even when filter means for removing leukocytes is used, the blood components collector unit having one satellite bag 4 as shown in FIG. 1 can also be used when two blood component layers, that is, the erythrocytes layer and the platelet-rich plasma layer, or the platelet-containing erythrocytes layer and the platelet-poor plasma layer, are intended to be obtained. When filter means for removing leukocytes is used and three blood component layers, namely the erythrocytes layer, the plasma layer and the platelets layer are intended to be obtained, at least two satellite bags 4, 5 are used (see FIGS. 2 and 8). In FIG. 2, a diagrammatic view is shown of another form of a blood components separator unit having two satellite bags, that is, first satellite bag 4 and second satellite bag 5. In FIG. 2, first satellite bag 4 is connected to primary bag 3 through third conduit means 10, and first satellite bag 4 in turn is connected to second satellite bag 5 through fourth conduit means 11. When the erythrocytes layer, the plasma layer and the platelet concentrate layer are intended to be obtained as blood components as described hereinbefore, a four-bag system is preferably used comprising first satellite bag 4, second satellite bag 5 and third satellite bag 24 (see FIG. 8). As shown in FIG. 8, third satellite bag 24 is connected to second satellite bag 5 through eighth conduit means 25.

The blood components separator unit may comprise physiologically isotonic solution-containing bag 6 which is connected to filter means 2 through sixth conduit means 12 branched from first conduit means 8 as shown in FIGS. 3 and 5, so that after passing whole blood through filter means 2, the physiologically isotonic solution may be passed through filter means 2 to complete the filtration of whole blood. Second valve means 14 is provided in sixth conduit means 12 so that the physiologically isotonic solution is prevented from flowing downward to filter means 2 before the operation of filtration of whole blood through filter means 2 is finished. Second valve means is operable by manual manipulation from outside of sixth conduit means 12. The same type of valve means as first valve means 20 mentioned hereinbefore can be used as second valve means 14. With respect to the physiologically isotonic solution, the same type of solution as described hereinbefore can be used.

The blood components separator unit of the present invention may comprise erythrocyte preservative-containing bag 7 (see FIG. 4). As the preservative for erythrocytes, the same type of preservative as described hereinbefore can be used. In FIG. 4, erythrocyte preservative bag 7 is connected to primary bag 3 and satellite bag 4 through seventh conduit means 13 and third conduit means 10. In operation, a suitable portion of conduit means 10 is pinched, for example by means of a clip so that the preservative may enter only the bag containing erythrocytes. Erythrocyte preservative bag 7 may alternatively be connected directly to primary bag 3 or satellite bag 4, which is used for collecting the erythrocytes. Third valve means 15 of the same type as first valve means 20 mentioned hereinbefore is provided in conduit means 13 so that the preservative is prevented from flowing downward before the blood is separated into blood components because the addition of the preservative to the bag containing blood components other than erythrocytes must be avoided. Third valve means 15 is operable by manual manipulation from outside of the seventh conduit means.

In the blood components separator unit of the present invention, each connection through each of the first to eighth conduit means 8, 9, 10, 11, 19, 12, 13 and 25 at both ends thereof is in a fixed fashion, thereby providing unified connections. Each connection may be attained by a customary method, for example, heat treatment, ultrasonication, adhesion by means of an adhesive, and the like. The connection may also be attained by forming the entire unit of the present invention integrally by molding as described, for example, in U.S. Pat. No. 3,946,731 and Japanese Patent Application Laid-Open Specification No. 54-113998.

The materials for primary bag 3, satellite bags 4, 5 and 24, blood collection bag 17, physiologically isotonic solution-containing bag 6, erythrocyte preservative-containing bag 7 are not critical, but it is preferred that each bag be made of a flexible material. Generally, polyvinyl chloride is used as a material. If the platelet-rich plasma or a platelet concentrate is intended to be collected as one of the blood components, it is preferred that at least the bag for collecting the platelet-rich plasma or a platelet concentrate be made of a material which well keeps the function of the platelets. Examples of such materials include a non-rigid polyvinyl chloride which has been treated with glow discharge, a material having high air-permeability and a polyolefin type elastomer. Especially, a material containing as a plasticizer a phthalic ester having a relatively large number of carbon atoms is preferred.

The shapes of the bags are also not critical. Generally, the shape of each bag may be rectangular, oval or the like. The capacities of blood collection bag 17, primary bag 3 and satellite bags 4, 5 and 24 are also not critical. Generally, the capacities of blood collection bag 17 and primary bag 3 may be about 200 to 600 ml, and the capacities of satellite bags 4, 5 and 24 may be about 100 to 400 ml.

The material of sealable, cuttable second conduit means 9 is as described hereinbefore. It is preferred that third conduit means 10, fourth conduit means 11 and eighth conduit means 25 also be made of the same sealable, cuttable material similar to the material of second; conduit means 9. The materials of first conduit means 8 and fifth to seventh conduit means 19, 12 and 13 are not critical and any material used for tubes in a conventional blood collection apparatus may be employed. Generally, polyvinyl chloride is used as a material for the conduit means. The conduit means may be flexible or rigid, which is appropriately chosen depending on the manner of operation of the unit.

The blood components separator unit of the present invention is in a sterile state. Such a sterile state may be attained by a conventional method. For example, the unit is sterilized by heat treatment, for example, by using an autoclave. Alternatively, the blood collector means, filter means, bags and conduit means are separately sterilized in the manner as described above and, then, they are aseptically connected by a conventional method to compose the blood components collector unit. With respect to the method for the aseptic connection, reference may be made to, for example, Japanese Patent Application Laid-Open Specification No. 62-8765 and the abstracts of the lectures published in The XXth Congress of The International Society of Blood Transfusion held on July 11-15, 1988, Nos. P-T-3-118 and P-T-3-122.

The blood components separator unit of the present invention is of a substantially closed system in which only the blood collector means is open to the outside at its open end, and the unit is sterilized entirely. Therefore, the unit can be used immediately without any preparatory operation.

According to the method of the present invention, whole blood taken from a donor can be aseptically and efficiently separated into two or more leukocyte-free blood components, such as leukocyte-free erythrocytes, leukocyte-free plasma, leukocyte-free platelets, leukocyte- and platelet-free erythrocytes and leukocyte- and platelet-free plasma. Therefore, the danger of not only the occurrence of hemolysis but also the formation of a microaggregate due to the presence of leukocytes can be avoided during the storage.

Further, according to the method of the present invention, the separation operation using a centrifuge is performed after the primary bag and the satellite bag system have been disconnected from the filter means for removing leukocytes or removing both leukocytes and platelets. Therefore, there is no danger that the filter means will be broken by the centrifugal operation or that the bags are ruptured by the friction between the filter means and the bags during the centrifugal operation.

The blood components separator unit of the present invention can advantageously be used for practicing the above-mentioned method for separating whole blood into blood components. By the use of the unit of the present invention, the above-mentioned method can be conducted aseptically with simple operation.

The present invention will now be described in more detail with reference to the following Examples which should not be construed to limit the scope of the present invention.

DETAILED DESCRIPTION OF THE PREFERRED EMBODIMENTS

In the following Examples, the leukocyte remaining ratio, the erythrocyte recovery and the platelet recovery after separating whole blood into blood components are determined by the following method.

Predetermined quantities of whole blood to be separated into blood components and respective blood components separated therefrom are taken as samples. An aliquot of each sample is diluted with Turk's solution and then subjected to a measurement of the leukocyte concentration by using a hemocytometer. Another aliquot is diluted 50,000 times with a dilution liquid (Cell Pack ®, sold by Toa Iryodenshi K.K., Japan) and subjected to a measurement of the erythrocyte concentration and the platelet concentration by using a microcell counter (Model F-800, sold by Toa Iryodenshi K.K., Japan). The leukocytes remaining ratio, the erythrocyte recovery and the platelet recovery are determined by the following equations.

$$\text{Leukocyte remaining ratio (\%)} = \frac{Q \times S}{P \times R} \times 100$$

wherein P is the volume of the whole blood, Q is the volume of each blood component, R is the leukocyte concentration of the whole blood and S is the leukocyte concentration of each blood component.

$$\text{Erythrocyte recovery (\%)} = \frac{Q \times U}{P \times T} \times 100$$

wherein P and Q have the same meanings as defined above, T is the erythrocyte concentration of the whole blood and U is the erythrocyte concentration of each blood component.

$$\text{Platelet recovery (\%)} = \frac{Q \times W}{P \times V} \times 100$$

wherein P and Q have the same meanings as defined above, V is the platelet concentration of the whole blood and W is the platelet concentration of each blood component.

EXAMPLE 1

A blood components separator unit comprising blood collector means 1, filter means 2 for removing both leukocytes and platelets, primary bag 3 and one satellite bag 4 as shown in FIG. 1 is used. Filter means 2 comprises three filtration media A, B and C, which are piled up to form a laminate. In filter means 2, the laminate is disposed in casing 21 to provide a first partition having blood inlet 22 and a second partition having blood outlet 23 as shown in FIG. 7.

The effective area of the laminate is 45 cm² (6.7 cm×6.7 cm). The effective area used herein means the area of a portion of the laminate through which the blood flows. Casing 21 of filter means 2 is made of an acrylonitrile-styrene copolymer resin. Filtration media A, B and C are each made of a non-woven fabric of polyester fibers. The fiber of filtration medium A has an average diameter of 1.65 μm. Filtration medium A has an average distance between two adjacent fibers of 3.1 μm and a thickness of 5.3 mm. The fiber of filtration medium B has an average diameter of 4 μm. Filtration medium B has an average distance between two adjacent fibers of 6.6 μm and a thickness of 2.5 mm. The fiber of filtration medium C has an average diameter of 25 μm. Filtration medium C has an average distance between two adjacent fibers of 40 μm and a thickness of 2.5 mm.

The average distance between two adjacent fibers (y) is determined by the following equation:

$$y = x \left( \sqrt{\frac{\pi}{2\sqrt{3}}} \cdot \sqrt{\frac{\rho}{D}} - 1 \right)$$

wherein y is the average distance between two adjacent fibers in microns; x is the average diameter of the fibers in microns; $\rho$ is the density of the fibers in g/cm³; D is the bulk density of the filtration medium in g/cm³; and $\pi$ is the ratio of the circumference of a circle to its diameter.

Blood collector means 1 comprises cannula 16 having a needle and, connected thereto through conduit means 19, blood collection bag 17 containing 56 ml of a CPD solution (anticoagulant 18), as shown in FIG. 6.

As primary bag 3 and satellite bag 4, polyvinyl chloride-made bags (manufactured and sold by Kawasumi Kagaku K.K., Japan) are used.

Using the above-mentioned blood components separator unit, whole blood is separated into blood components as follows.

First, 400 g of whole blood is collected from a donor into blood collection bag 17 through cannula 16 and conduit means 19. During the blood collection operation, first conduit means 8 disposed between blood collector means 1 and filter means 2 is closed by means of valve means 20 (see FIG. 6). The valve means is operable by manual manipulation from outside of first conduit means 8 for opening the valve means, thereby enabling the collected blood in blood collection bag 17 to flow down into filter means 2. After 400 g of whole blood is collected from the donor into blood collection bag 17, cannula 16 is taken off from the vein of the donor, and then the tip of the cannula is sealed with a cap (which is not shown in FIG. 6). The collected whole blood is mixed with 56 ml of the CPD solution contained in blood collection bag 17. To mix the anticoagulant and blood cells, blood collection bag 17 is manually shaken or inverted.

Then, valve means 20 is opened, thereby allowing the CPD-containing whole blood in blood collection bag 17 to flow downward into filter means 2 by the force of gravity. The leukocytes and platelets in the whole blood are removed by filter means 2 and the filtered blood passes into primary bag 3. Completion of filtration of the collected whole blood by filter means 2 takes about 20 minutes.

Then, conduit means 9 is sealed at two portions intermediate the length thereof by a heat sealer. Next, conduit means 9 is cut at a portion between two sealed portions by means of scissors to thereby disconnect from filter means 2 primary bag 3 containing the filtered blood and satellite bag 4 which is connected to primary bag 3 through conduit means 10. The thus separated primary bag 3 containing the filtered blood and satellite bag 4 are subjected to centrifugation at 3000×g, at 4° C. for 6 minutes by means of a centrifuge. Then, primary bag 3 and satellite bag 4 are taken out of the centrifuge and the upper plasma layer is transferred into satellite bag 4 from primary bag 3 by externally applying pressure to primary bag 3 using a separation stand (manufactured and sold by Terumo Corp., Japan).

Thus, the leukocyte- and platelet-removed erythrocytes are obtained in primary bag 3 and the leukocyte- and platelet-removed plasma is obtained in satellite bag 4. The erythrocyte recovery and the leukocyte remaining ratio are determined in the manner mentioned above.

As a result, it is found that the erythrocyte recovery and the leukocytes remaining ratio in the erythrocytes collected in primary bag 3 are 90% and 0.9%, respectively. In satellite bag 4, 168 ml of the plasma are collected.

During the blood components separation operation, the primary bag, the satellite bag and the conduit means of the blood components separator unit are not damaged.

EXAMPLE 2

A blood components collector unit comprising blood collector means 1, filter means 2 for removing leukocytes, primary bag 3 and two satellite bags 4 and 5 is used (see FIG. 2).

Filter means 2 for removing only leukocytes is prepared as follows. A copolymer of 2-hydroxyethyl methacrylate (hereinafter referred to as "HEMA") and diethylaminoethyl methacrylate (hereinafter referred to as "DEAMA") (HEMA:DEAMA=95:5, by mole) is synthesized by a customary solution radical polymerization. That is, the HEMA and DEAMA are dissolved in ethanol in amounts of 0.95 mole/l and 0.05 mole/l, respectively. To the resultant mixture, 1/200 mole/l of azoisobutylonitrile is added as an initiator. Polymerization is conducted at 60° C. for 8 hours to form a copolymer. Then, the reaction mixture is dropped into distilled water to precipitate the copolymer and the precipitated copolymer is lyophilized, to thereby obtain a purified copolymer. The thus obtained copolymer is dissolved in ethanol at a concentration of 1 g/dl to obtain a copolymer solution.

On the other hand, a non-woven fabric of polyethylene terephthalate fibers having an average diameter of 1.8 μm is cut into squares having a size of 67 mm×67 mm to form square sheets. A plurality of square sheets are piled up to form a laminate so that the thickness of the laminate is 7 mm, and the laminate sheets are packed in the same casing 21 as shown in FIG. 7. Then, the above-obtained copolymer solution is passed through the laminate sheets in the casing and the surplus of the copolymer solution contained in the laminate sheets is removed by blowing the sheets with dry nitrogen gas to dryness. The laminate sheets are dried well for 16 hours in vacuo, to thereby obtain filter means 2 for removing leukocytes. The filtration medium of the thus prepared filter means has an effective cross-sectional area of 3600 mm² (60 mm×60 mm), a thickness of 7 mm and a weight of 4.2 g.

Blood collector means 1 comprises cannula 16 having a needle and, connected thereto, a blood collection bag 17 containing 56 ml of a CPD solution as shown in FIG. 6. As primary bag 3 and satellite bags 4 and 5, polyvinyl chloride-made bags (manufactured and sold by Kawasumi Kagaku K.K., Japan) are used.

Using the above-obtained blood components collector unit, whole blood is separated into blood components as follows.

First, 400 g of whole blood is collected in blood collection bag 17 to mix whole blood with an anticoagulant in substantially the same manner as in Example 1. The collected whole blood is passed downward into filter means 2 for removing leukocytes. The leukocyte-removed filtered blood is passed into primary bag 3. Completion of filtration takes about 20 min.

Then, conduit means 9 is sealed at two portions intermediate the length thereof by means of a heat sealer. Then, conduit means 9 is cut at a portion between the sealed two portions by means of scissors to disconnect, from filter means 2, primary bag 3 containing the filtered blood and satellite bags 4 and 5 which are fluid-tightly connected to primary bag 3. Bags 3, 4 and 5 are subjected to centrifugation at 300×g, at 22° C. for 18 minutes using a centrifuge. Thus, the filtered blood in primary bag 3 is separated into the erythrocytes which assumes a lower layer and a mixture of the plasma and the platelets which assumes an upper layer.

Bags 3, 4 and 5 are taken out of the centrifuge and the upper layer in primary bag 3 is transferred into satellite bag 4 by externally applying pressure to primary bag 3 using a separation stand (manufactured and sold by Terumo Corp., Japan). Then, primary bag 3 and satellite bags 4 and 5 are subjected to centrifugation at 3000×g, at 22° C. for 6 minutes by a centrifuge. Thus, the mixture is separated into the plasma which assumes an upper layer and the platelets which assume a lower layer in satellite bag 4. Primary bag 3 and satellite bags 4 and 5 are taken out of the centrifuge and a major portion of the plasma in satellite bag 4 is transferred into satellite bag 5 by applying pressure satellite bag 4 using a separation stand (manufactured and sold by Terumo Corp., Japan), leaving 20 ml of the plasma in satellite bag 4.

With respect to the thus obtained blood components, the leukocyte remaining ratio, the erythrocyte recovery and the platelet recovery are determined in the same manner as described hereinbefore.

As a result, it is found that the erythrocyte recovery and the leukocytes remaining ratio in the separated erythrocytes collected in primary bag 3 are 91% and 0.8%, respectively. The platelet recovery and the leukocytes remaining ratio in the separated platelets collected in satellite bag 4 are 62% and 0.9%, respectively. In satellite bag 5, 164 ml of the plasma are collected.

During the blood components separation operation, the primary bag, the satellite bags and conduit means of the blood components separator unit are not damaged.

EXAMPLE 3

A blood components separator unit as shown in FIG. 3 is used. The unit is substantially the same as the unit used in Example 1 except that physiologically isotonic solution-containing bag 6 is connected to filter means 2 through conduit means 12 branched from conduit means 8. Physiologically isotonic solution-containing bag 6 is made of polyvinyl chloride and contains 50 ml of a physiological saline.

Using the blood components separator unit, substantially the same procedure as in Example 1 is repeated except that the physiological saline in physiologically isotonic solution-containing bag 6 is passed through filter means 2 to complete the filtration of the whole blood.

With respect to the thus obtained blood components, the leukocyte remaining ratio and the erythrocyte recovery are determined in the same manner as described hereinbefore.

As a result, it is found that the erythrocyte recovery and the leukocytes remaining ratio in the separated erythrocytes-collected in primary bag 3 are 96% and 0.7%, respectively. In satellite bag 4, 180 ml of the plasma.

During the blood components separation operation, primary bag 3, satellite bag 4 and conduit means 10 of the blood components separator unit are not damaged.

As apparent from the results, by passing the physiologically isotonic solution through the filter means, the erythrocyte recovery and plasma recovery are increased as compared to those in Example 1.

EXAMPLE 4

A blood components separator unit as shown in FIG. 5 is used. The unit is substantially the same as the unit used in Example 2 except that physiologically isotonic solution-containing bag 6 is connected to filter means 2 through conduit means 12 branched from conduit means 8. Physiologically isotonic solution-containing bag 6 is made of polyvinyl chloride and contains 30 ml of a physological saline.

Using the blood components separator unit, substantially the same procedure as in Example 2 is repeated except that the physiological saline in physiologically isotonic solution-containing bag 6 is passed through filter means 2 to complete the filtration of the whole blood.

With respect to the thus obtained blood components, the leukocyte remaining ratio, the erythrocyte recovery and the platelet recovery are determined in the same manner as described hereinbefore.

As a result, it is found that the erythrocyte recovery and the leukocytes remaining ratio of the separated erythrocytes-collected in primary bag 3 are 96% and 0.8%, respectively. The platelet recovery and the leukocytes remaining ratio of the separated platelets collected in satellite bag 4 are 66% and 0.9%, respectively. In satellite bag 5, 178 ml of the plasma are collected.

During the blood components separation operation, primary bag 3, satellite bags 4 and 5 and conduit means 10 and 11 of the blood components separator unit are not damaged.

As apparent from the results, by passing the physiologically isotonic solution through the filter means, the erythrocyte recovery, platelet recovery and plasma recovery are increased as compared to those in Example 2.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for separating blood into blood components, comprising the steps of:
   (a) providing blood collector means fluid-tightly connected to filter means for removing leukocytes or removing leukocytes and platelets from whole blood, said filter means being fluid-tightly connected to a primary bag through sealable, cuttable conduit means;
   (b) collecting, from a donor, whole blood comprising plasma, erythrocytes, leukocytes and platelets;
   (c) passing the whole blood through said filter means to produce a filtered blood containing the plasma, the erythrocytes and the platelets or containing the plasma and the erythrocytes;
   (d) discharging the filtered blood from said filter means into said primary bag through said conduit means;
   (e) sealing said conduit means at least at one portion intermediate ends thereof;
   (f) cutting said conduit means portion to separate said conduit means into a filter means-side unsealed or sealed conduit portion and a primary bag-side sealed conduit portion to thereby disconnect from said filter means said primary bag containing the filtered blood, said disconnected primary bag being sealed by virtue of said primary bag-side sealed conduit portion connected to said primary bag; and
   (g) centrifuging the filtered blood in said primary bag.

2. The method according to claim 1, wherein in step (c), the whole blood is passed through said filter means for removing leukocytes, and in step (g), the filtered blood is separated into an erythrocytes layer and a mixture layer of the plasma and the platelets, and following step (g), said mixture layer is subsequently subjected to centrifugation to separate said mixture layer into a plasma layer and a platelets layer.

3. The method according to claim 1, wherein in step (c), the whole blood is passed through said filter means for removing leukocytes, and in step (g), the filtered blood is separated into an erythrocytes layer, a plasma layer and a platelets layer, and following step (g), two of said layers are individually separated from the remainder to obtain the separated erythrocytes layer, the separated plasma layer and the separated platelets layer so that the separated platelets layer contains a small amount of the plasma and a small amount of the erythrocytes, but the separated erythrocytes layer and the separated plasma layer consist substantially of the erythrocytes and the plasma, respectively, and the separated platelets layer containing a small amount of the plasma and a small amount of the erythrocytes is separated into the erythrocytes and a platelet concentrate containing the platelets and the plasma.

4. The method according to claim 1, wherein in step (c), the whole blood is passed through said filter means for removing leukocytes and platelets, and in step (g), the filtered blood is separated into the erythrocytes and the plasma.

5. The method according to any one of claims 1 to 4, wherein said blood collector means comprises a blood collection bag containing an anticoagulant, so that step (b) further comprises the step of mixing the whole blood with said anticoagulant.

6. The method according to any one of claims 1 to 4, further comprising, following step (d) and prior to step (e), the step of passing a physiologically isotonic solution through said filter means to complete filtration of the whole blood by said filter means.

7. The method according to any one of claims 1 to 4, further comprising, following step (g), the step of adding a preservative for erythrocytes to the separated erythrocytes.

8. A blood components separator unit comprising:
   means for collecting blood comprising plasma, erythrocytes, leukocytes and platelets;
   filter means for selectively removing leukocytes while passing plasma, erythrocytes and platelets therethrough, or removing leukocytes and platelets while passing plasma and erythrocytes therethrough, said filter means having an inlet for blood collected through said means for collecting blood and a filtrate outlet for filtered blood comprising plasma, erythrocytes and platelets substantially free from leukocytes, or comprising plasma and erythrocytes substantially free from leukocytes and platelets;
   first conduit means for connecting the means for collecting blood to the inlet of said filter means;
   a primary bag;
   second conduit means for connecting the filtrate outlet of said filter means to said primary bag, said second conduit means being sealable and cuttable;
   a satellite bag system; and
   additional conduit means for connecting the satellite bag system to sad primary bag, the additional conduit means being sealable and cuttable,
   wherein connections of the first conduit means between the means for collecting blood and the inlet of said filter means, connections of the second conduit means between the filtrate outlet for filtered blood and primary bag and connections of the additional conduit means between the primary bag and satellite bag system are fixed, thereby providing unified connections.

9. The blood components separator unit according to claim 8, wherein said satellite bag system comprises one satellite bag and third conduit means for connecting the one satellite bag to said primary bag.

10. The blood components separator unit according to claim 8, wherein said satellite bag system comprises a first satellite bag and a second satellite bag, and further comprising:
   third conduit means for connecting said first satellite bag to said primary bag; and
   fourth conduit means for connecting said second satellite bag to said first satellite bag or said third conduit means.

11. The blood components separator unit according to any one of claims 8 to 10, wherein said filter means selectively removes leukocytes while passing plasma, erythrocytes and platelets therethrough, and said filtered blood comprises plasma, erythrocytes and platelets substantially free from leukocytes.

12. The blood components separator unit according to any one of claims 8 to 10, wherein said filter means selectively removes leukocytes and platelets while passing plasma and erythrocytes therethrough, and said filtered blood comprises plasma and erythrocytes substantially free from leukocytes and platelets.

13. A blood components separator unit comprising:
   means for collecting blood comprising plasma, erythrocytes, leukocytes and platelets, said means for collecting blood comprising a cannula and a blood collection bag containing an anticoagulant;
   filter means for selectively removing leukocytes while passing plasma, erythrocytes and platelets therethrough, or removing leukocytes and platelets while passing plasma and erythrocytes therethrough, said filter means having an inlet for blood collected through said means for collecting blood and a filtrate outlet for filtered blood comprising plasma, erythrocytes and platelets substantially free from leukocytes, or comprising plasma and erythrocytes substantially free from leukocytes and platelets;
   first conduit means for connecting the means for collecting blood to the inlet of said filter means;
   a primary bag;
   second conduit means for connecting the filtrate outlet of said filter mean s to said primary bag, said second conduit means being sealable and cuttable;
   fifth conduit means for connecting said blood collection bag to said cannula, said blood collection bag also being connected to said filter means through said first conduit means;
   first valve means in said first conduit means for controlling flow therethrough, said first valve means being operable by manual manipulation outside of said first conduit means;
   a satellite bag system; and
   additional conduit means for connecting the satellite bag system to said primary bag, said additional conduit means being sealable and cuttable;
   wherein connections of the first conduit means between the means for collecting blood and the inlet of said filter means, connections for the second conduit means between the filtrate outlet for filtered blood and primary bag, connections of the fifth conduit means between the blood collection bag and cannula and connections of the additional conduit means between the primary bag and satellite bag system are fixed, thereby providing unified connections.

14. The blood components separator unit according to claim 13, wherein said satellite bag system comprises one satellite bag and third conduit means for connecting the one satellite bag to said primary bag.

15. The blood components separator unit according to claim 13, wherein said satellite bag system comprises a first satellite bag and a second satellite bag, and further comprising:
   third conduit means for connecting said first satellite bag to said primary bag; and
   fourth conduit means for connecting said second satellite bag to said first satellite bag or said third conduit means.

16. The blood components separator unit according to claim 13, wherein said satellite bag system comprises a first satellite bag, a second satellite bag and a third satellite bag, and further comprising:
   third conduit means for connecting said first satellite bag to said primary bag;
   fourth conduit means for connecting said second satellite bag to said first satellite bag or said third conduit means; and
   eighth conduit means for connecting said third satellite bag to said second satellite bag or said fourth conduit means.

17. A blood components separator unit comprising:
   means for collecting blood comprising plasma, erythrocytes, leukocytes and platelets;
   filter means for selectively removing leukocytes while passing plasma, erythrocytes and platelets therethrough, or removing leukocytes and platelets while passing plasma and erythrocytes therethrough, said filter means having an inlet for blood collected through said means for collecting blood and a filtrate outlet for filtered blood comprising plasma, erythrocytes and platelets substantially free from leukocytes, or comprising plasma and erythrocytes substantially free from leukocytes and platelets;
   first conduit means for connecting the means for collecting blood to the inlet of said filter means;
   a primary bag;
   second conduit means for connecting the filtrate outlet of said filter means to said primary bag, said second conduit means being sealable and cuttable;
   a physiologically isotonic solution-containing bag;
   sixth conduit means for connecting said physiologically isotonic solution-containing bag to said filter means, said sixth conduit means being branched from said first conduit means; and
   second valve means in said sixth conduit means for controlling flow therethrough, said second valve means being operable by manual manipulation outside of said sixth conduit means;
   a satellite bag system; and
   additional conduit means for connecting the satellite bag system to said primary bag, said additional conduit means being sealable and cuttable;
   wherein connections of the first conduit means between the means for collecting blood and the inlet of said filter means, connections of the second conduit means between the filtrate outlet for filtered blood and primary bag, connections of the sixth conduit means between the physiologically isotonic solution containing bag and first conduit means and connections of the additional conduit means between the primary bag and satellite bag system are fixed, thereby providing unified connections.

18. The blood components separator unit according to claim 17, wherein said satellite bag system comprises one satellite bag and third conduit means for connecting the one satellite bag to said primary bag.

19. The blood components separator unit according to claim 17, wherein said satellite bag system comprises a first satellite bag and a second satellite bag, and further comprising:
 third conduit means for connecting said first satellite bag to said primary bag; and
 fourth conduit means for connecting said second satellite bag to said first satellite bag or said third conduit means.

20. The blood components separator unit according to claim 17, wherein said satellite bag system comprises a first satellite bag, a second satellite bag and a third satellite bag, and further comprising:
 third conduit means for connecting said first satellite bag to said primary bag;
 fourth conduit means for connecting said second satellite bag to said first satellite bag or said third conduit means; and
 eighth conduit means for connecting said third satellite bag to said second satellite bag or said fourth conduit means.

21. A blood components separator unit comprising:
 means for collecting blood comprising plasma, erythrocytes, leukocytes and platelets;
 filter means for selectively removing leukocytes while passing plasma, erythrocytes and platelets therethrough, or removing leukocytes and platelets while passing plasma and erythrocytes therethrough, said filter means having an inlet for blood collected through said means for collecting blood and a filtrate outlet for filtered blood comprising plasma, erythrocytes and platelets substantially free from leukocytes, or comprising plasma and erythrocytes substantially free from leukocytes and platelets;
 first conduit means for connecting the means for collecting blood to the inlet of said filter means;
 a primary bag;
 second conduit means for connecting the filtrate outlet of said filter means to said primary bag, said second conduit means being sealable and cuttable;
 an erythrocyte preservative-containing bag;
 seventh conduit means for connecting said erythrocyte preservative-containing bag to at least one of said primary bag, said satellite bag and said third conduit means; and
 third valve means in said seventh conduit means for controlling flow therethrough, said third valve means being operable by manual manipulation outside of said seventh conduit means;
 a satellite bag system; and
 additional conduit means for connecting the satellite bag system top said primary bag, said additional conduit means being sealable and cuttable;
 wherein connections of the first conduit means between the means for collecting blood and the inlet of said filter means, connections of the second conduit means between the filtrate outlet for filtered blood and primary bag, connections of the seventh conduit means between the erythrocyte preservative-containing bag and at least one of the primary bag, satellite bag system and additional conduit means and connections of the additional conduit means between the primary bag and satellite bag system are fixed, thereby providing unified connections.

22. The blood components separator unit according to claim 21, wherein said satellite bag system comprises one satellite bag and third conduit means for connecting the one satellite bag to said primary bag.

23. The blood components separator unit according to claim 21, wherein said satellite bag system comprises a first satellite bag and a second satellite bag, and further comprising:
 third conduit means for connecting said first satellite bag to said primary bag; and
 fourth conduit means for connecting said second satellite bag to said first satellite bag or said third conduit means.

24. The blood components separator unit according to claim 21, wherein said satellite bag system comprises a first satellite bag, a second satellite bag and a third satellite bag, and further comprising:
 third conduit means for connecting said first satellite bag to said primary bag;
 fourth conduit means for connecting said second satellite bag to said first satellite bag or said third conduit means; and
 eighth conduit mean s for connecting said third satellite bag to said second satellite bag or said fourth conduit means.

* * * * *

US004985153C1

(12) EX PARTE REEXAMINATION CERTIFICATE (5265th)
United States Patent
Kuroda et al.

(10) Number: US 4,985,153 C1
(45) Certificate Issued: Feb. 7, 2006

(54) METHOD FOR SEPARATING BLOOD INTO BLOOD COMPONENTS, AND BLOOD COMPONENTS SEPARATOR UNIT

(75) Inventors: Toru Kuroda, Oita (JP); Takao Nishimura, Oita (JP)

(73) Assignee: Asahi Medical Co., Ltd., Tokyo (JP)

Reexamination Request:
No. 90/006,682, Jun. 24, 2003

Reexamination Certificate for:
Patent No.: 4,985,153
Issued: Jan. 15, 1991
Appl. No.: 07/370,750
Filed: Jun. 23, 1989

(30) Foreign Application Priority Data

Jun. 23, 1988 (JP) .......................................... 63-153464
Jun. 23, 1988 (JP) .......................................... 63-153465

(51) Int. Cl.
*B01D 21/26* (2006.01)
*B01D 36/00* (2006.01)
*B01D 37/00* (2006.01)

(52) U.S. Cl. .................... 210/782; 210/206; 210/496; 210/767; 210/789; 210/806; 494/37; 604/406; 604/410

(58) Field of Classification Search .............. 210/206, 210/252, 257.1, 496, 767, 782, 787, 789, 210/806; 494/37; 604/406, 408, 410
See application file for complete search history.

(56) References Cited

U.S. PATENT DOCUMENTS

| | | | | |
|---|---|---|---|---|
| 3,870,042 | A | * | 3/1975 | Viguier ........................ 604/406 |
| 4,330,410 | A | * | 5/1982 | Takenaka et al. ............ 210/767 |
| 4,369,779 | A | | 1/1983 | Spencer |
| 4,512,763 | A | | 4/1985 | Schneider |
| 4,596,657 | A | | 6/1986 | Wisdom |
| 4,608,178 | A | | 8/1986 | Johansson et al. |
| 4,701,267 | A | | 10/1987 | Watanabe et al. |
| 4,767,541 | A | * | 8/1988 | Wisdom ...................... 210/787 |
| 4,810,378 | A | * | 3/1989 | Carmen et al. ............. 210/206 |
| 4,898,573 | A | * | 2/1990 | Takenaka et al. .......... 604/6.04 |
| 4,985,153 | A | * | 1/1991 | Kuroda et al. .............. 210/782 |

FOREIGN PATENT DOCUMENTS

| | | | |
|---|---|---|---|
| EP | 0155003 | * | 9/1985 |
| EP | 0266683 | * | 5/1988 |
| EP | 0 267 286 A1 | | 5/1988 |
| GB | 1 516 698 | | 7/1978 |
| JP | 55-129755 | * | 10/1980 |
| WO | WO 84/00892 | | 3/1984 |

OTHER PUBLICATIONS

"Advanced Methods for Leukocyte Removal by Blood Filtration", Abstract from Int'l. Workshop on the Role of Leucocyte Depletion in Blood Transfusion Practice by T. Nishimura et al., Jul. 9, 1988, pp. 18–19.*

"Use of Sterile Connecting Device to Prepare Leukocyte–Poor Filtered Red Cells in a Closed System", Abstract from Int'l Workshop on the Role of Leucocyte Depletion in Blood Transfusion Practice by J. James et al., Jul. 9, 1988, pp. 24–25.*

(Continued)

*Primary Examiner*—Joseph Drodge

(57) ABSTRACT

A method for separating blood into blood components aseptically in a closed system first filters whole blood through a filter for removing leukocytes or removing leukocytes and platelets, to produce filtered blood, which is passed to and collected in a primary bag fluid-tightly connected to the filter through a sealable, cuttable conduit, and the conduit is sealed and cut to disconnect the primary bag from the filter. The disconnected primary bag is subjected to centrifugation to separate the filtered blood into blood components. The method is useful for separately collecting leukocyte-removed blood components, particularly leukocyte-removed erythrocytes, leukocyte-removed plasma, leukocyte-removed platelets, etc., from the whole blood of a healthy human. A blood components separation unit which can advantageously be used in the practice of the above method is also disclosed.

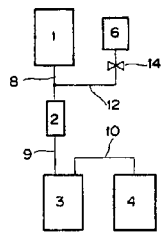

OTHER PUBLICATIONS

"35 Days Storage of Leucocyte Free Red Blood Cells Concentrates: In Vitro Study", Abstract from Int'l Workshop on the Role of Leucocyte Depletion in Blood Transfusion Practice by M. Angue et al., Jul. 9, 1988, p. 46.*

Frey–Wettstein et al., *Vox Sanguinis* vol. 27, No. 1 21–28 (1974).

Perkins et al., *Transfusion* vol. 13, No. 4 194–199 (1973).

Miller et al., *Transfusion* vol. 13, No. 4 189–193 (1973).

Diepenhorst, *Removal of Leukocytes from Blood by Filtration though Cotton Wool* 13–19 (1974).

English translation of pp. 43 and 44 of the Operation Standards of the Red Cross Center, Technical Section, Japan Red Cross Blood Department (1979).

English Translation of Decision of Japanese Board of Appeals in nullification action No. 2000–35352 filed against Japanese Patent No. 1930016 (Nov. 26, 2002).

$2^{nd}$ Instance Decision (Court of Appeals) and Decision from the House of Lords regarding the validity of European Patent No. 0 349 188 in Great Britain (2002).

Decision from the Court of the First Instance of Paris regarding the validity of European Patent No. 0 349 188 in Paris (2002).

* cited by examiner

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the
patent, but has been deleted and is no longer a part of the
patent; matter printed in italics indicates additions made
to the patent.

AS A RESULT OF REEXAMINATION, IT HAS BEEN
DETERMINED THAT:

Claims 1–3, 8–11 and 13–24 are cancelled.

Claims 4–7 and 12 are determined to be patentable as amended.

New claims 25–62 are added and determined to be patentable.

4. [The method according to claim 1, wherein in step (c),] *A method for separating blood into blood components, comprising the steps of:*
  (a) *providing blood collector means fluid-tightly connected to filter means for removing leukocytes and platelets from whole blood, said filter means being fluid-tightly connected to a primary bag through sealable, cuttable conduit means;*
  (b) *collecting, from a donor, whole blood comprising plasma, erythrocytes, leukocytes and platelets;*
  (c) *passing* the whole blood [is passed] through said filter means for removing leukocytes and platelets, [and in step (g),] *to produce a filtered blood substantially free of leukocytes and containing the plasma and the erythrocytes;*
  (d) *discharging the filtered blood from said filter means into said primary bag through said conduit means;*
  (e) *sealing said conduit means at least at one portion intermediate to the ends thereof;*
  (f) *cutting said conduit means portion to separate said conduit means into a filter means-side unsealed or sealed conduit portion and a primary bag-side sealed conduit portion to thereby disconnect from said filter means said primary bag containing the filtered blood, said disconnected primary bag being sealed by virtue of said primary bag-side sealed conduit portion connected to said primary bag; and*
  (g) *centrifuging the filtered blood in said primary bag, wherein* the filtered blood is separated into the erythrocytes and the plasma.

5. The method according to [any one of claims 1 to] *claim* 4, wherein said blood collector means comprises a blood collection bag containing an anticoagulant, so that step (b) further comprises the step of mixing the whole blood with said anticoagulant.

6. The method according to [any one of claims 1 to] *claim* 4, further comprising, following step (d) and prior to step (e), the step of passing a physiologically isotonic solution through said filter means to complete filtration of the whole blood by said filter means.

7. The method according to [any one of claims 1 to] *claim* 4, further comprising, following step (g), the step of adding a preservative for erythrocytes to the separated erythrocytes.

12. [The blood components separator unit according to any one of claims 8 to 10, wherein said] *A blood components separator unit comprising:*
  *means for collecting blood comprising plasma, erythrocytes, leukocytes and platelets;*
  filter means *for* selectively [removes]*removing* leukocytes and platelets while passing plasma and erythrocytes therethrough, [and] said *filter means having an inlet for blood collected through said means for collecting blood and a filtrate outlet for* filtered blood [comprises]*comprising* plasma and erythrocytes substantially free from leukocytes and platelets;
  *first conduit means for connecting the means for collecting blood to the inlet of said filter means;*
  *a primary bag;*
  *second conduit means for connecting the filtrate outlet of said filter means to said primary bag, said second conduit means being sealable and cuttable;*
  *a satellite bag system; and*
  *additional conduit means for connecting the satellite bag system to said primary bag, the additional conduit means being sealable and cuttable,*
  *wherein connections of the first conduit means between the means for collecting blood and the inlet of said filter means, connections of the second conduit means between the filtrate outlet for filtered blood and primary bag and connections of the additional conduit means between the primary bag and satellite bag system are fixed, thereby providing unified connections.*

25. *The method of claim 4, wherein the blood collector means, primary bag, conduit means and filter are parts of a blood component separator unit, which is a substantially closed system that is only open to the outside where the blood collector means collects blood from a donor.*

26. *The method of claim 4, wherein said primary bag is connected to a satellite bag system having at least one satellite bag through sealable, cuttable conduit means; and further comprising*
  (h) *transferring one or more blood components to said satellite bag system to obtain, separately from each other, plasma and erythrocytes,*
  *whereby plasma suitable for transfusion and erythrocytes suitable for transfusion are obtained.*

27. *The method of claim 4, wherein said blood components are separated aseptically.*

28. *The blood components separator according to claim 12, wherein said blood component separator unit is a substantially closed system that is only open to the outside where the blood collector means collects blood from the donor.*

29. *The blood components separator unit of claim 28, wherein said filtered blood contains less than 1.0% leukocytes.*

30. *The blood components separator unit according to claim 12, wherein said blood components separator unit aseptically separates whole blood into plasma suitable for transfusion and erythrocytes suitable for transfusion.*

31. *The blood components separator unit of claim 30, wherein said blood component separator unit is a substantially closed system that is only open to the outside where the blood collector means collects blood from the donor.*

32. *The blood components separator unit according to claim 12, wherein said satellite bag system comprises one satellite bag and third conduit means for connecting the one satellite bag to said primary bag.*

33. The blood components separator unit according to claim 12, wherein said satellite bag system comprises a first satellite bag and a second satellite bag, and further comprising:
   third conduit means for connecting said first satellite bag to said primary bag; and
   fourth conduit means for connecting said second satellite bag to said first satellite bag or said third conduit means.

34. The blood components separator unit according to claim 12, wherein said means for collecting blood comprises a cannula and a blood collection bag containing an anticoagulant; and said separator unit further comprises:
   fifth conduit means for connecting said blood collection bag to said cannula, said blood collection bag also being connected to said filter means through said first conduit means;
   first valve means in said first conduit means for controlling flow therethrough, said first valve means being operable by manual manipulation outside of said first conduit means; and
   wherein connections of the first conduit means between the means for collecting blood and the inlet of said filter means, connections for the second conduit means between the filtrate outlet for filtered blood and primary bag, connections of the fifth conduit means between the blood collection bag and cannula and connections of the additional conduit means between the primary bag and satellite bag system are fixed, thereby providing unified connections.

35. The blood components separator unit according to claim 34, wherein said satellite bag system comprises one satellite bag and third conduit means for connecting the one satellite bag to said primary bag.

36. The blood components separator unit according to claim 34, wherein said satellite bag system comprises a first satellite bag and a second satellite bag, and further comprising:
   third conduit means for connecting said first satellite bag to said primary bag; and
   fourth conduit means for connecting said second satellite bag to said first satellite bag of said third conduit means.

37. The blood components separator unit according to claim 34, wherein said satellite bag system comprises a first satellite bag, a second satellite bag and a third satellite bag, and further comprising:
   third conduit means for connecting said first satellite bag to said primary bag;
   fourth conduit means for connecting said second satellite bag to said first satellite bag or said third conduit means; and
   eighth conduit means for connecting said third satellite bag to said second satellite bag or said fourth conduit means.

38. The blood components separator unit according to claim 12, further comprising:
   a physiologically isotonic solution-containing bag;
   sixth conduit means for connecting said physiologically isotonic solution-containing bag to said filter means, said sixth conduit means being branched from said first conduit means; and
   second valve means in said sixth conduit means for controlling flow therethrough, said second valve means being operable by manual manipulation outside of said sixth conduit means; and
   wherein connections of the first conduit means between the means for collecting blood and the inlet of said filter means, connections of the second conduit means between the filtrate outlet for filtered blood and primary bag, connections of the sixth conduit means between the physiologically isotonic solution containing bag and first conduit means and connections of the additional conduit means between the primary bag and satellite bag system are fixed, thereby providing unified connections.

39. The blood components separator unit according to claim 38, wherein said satellite bag system comprises one satellite bag and third conduit means for connecting the one satellite bag to said primary bag.

40. The blood components separator unit according to claim 38, wherein said satellite bag system comprises a first satellite bag and a second satellite bag, and further comprising:
   third conduit means for connecting said first satellite bag to said primary bag; and
   fourth conduit means for connecting said second satellite bag to said first satellite bag or said third conduit means.

41. The blood components separator unit according to claim 38, wherein said satellite bag system comprises a first satellite bag, a second satellite bag and a third satellite bag, and further comprising:
   third conduit means for connecting said first satellite bag to said primary bag;
   fourth conduit means for connecting said second satellite bag to said first satellite bag or said third conduit means; and
   eighth conduit means for connecting said third satellite bag to said second satellite bag or said fourth conduit means.

42. The blood components separator unit according to claim 12, further comprising:
   an erythrocyte preservative-containing bag;
   seventh conduit means for connecting said erythrocyte preservative-containing bag to at least one of said primary bag, said satellite bag and said third conduit means; and
   third valve means in said seventh conduit means for controlling flow therethrough, said third valve means being operable by manual manipulation outside of said seventh conduit means;
   wherein connections of the first conduit means between the means for collecting blood and the inlet of said filter means, connections of the second conduit means between the filtrate outlet for filtered blood and primary bag, connections of the seventh conduit means between the erythrocyte preservative-containing bag and at least one of the primary bag, satellite bag system and additional conduit means and connections of the additional conduit means between the primary bag and satellite bag system are fixed, thereby providing unified connections.

43. The blood components separator unit according to claim 42, wherein said satellite bag system comprises one satellite bag and third conduit means for connecting the one satellite bag to said primary bag.

44. The blood components separator unit according to claim 42, wherein said satellite bag system comprises a first satellite bag and a second satellite bag, and further comprising:
   third conduit means for connecting said first satellite bag to said primary bag; and fourth conduit means for connecting said second satellite bag to said first satellite bag or said third conduit means.

45. The blood components separator unit according to claim 42, wherein said satellite bag system comprises a first satellite bag, a second satellite bag and a third satellite bag, and further comprising:
  third conduit means for connecting said first satellite bag to said primary bag;
  fourth conduit means for connecting said second satellite bag to said first satellite bag or said third conduit means; and
  eighth conduit means for connecting said third satellite bag to said second satellite bag or said fourth conduit means.

46. A method for separating blood into blood components, comprising the steps of:
  (a) providing blood collector means fluid-tightly connected to filter means for removing leukocytes and platelets from whole blood, said filter means being fluid-tightly connected to a primary bag through sealable, cuttable conduit means;
  (b) collecting, from a donor, whole blood comprising plasma, erythrocytes, leukocytes and platelets;
  (c) passing the whole blood through said filter means for removing leukocytes and platelets to produce a filtered blood containing the plasma and the erythrocytes and less than 1.0% leukocytes;
  (d) discharging the filtered blood from said filter means into said primary bag through said conduit means;
  (e) sealing said conduit means at least at one portion of the intermediate ends thereof;
  (f) cutting said conduit means portion to separate said conduit means into a filter means-side unsealed or sealed conduit portion and a primary bag-side sealed conduit portion to thereby disconnect from said filter means said primary bag containing the filtered blood, said disconnected primary bag being sealed by virtue of said primary bag-side sealed conduit portion connected to said primary bag; and
  (g) centrifuging the filtered blood in said primary bag, wherein the filtered blood is separated into the erythrocytes and the plasma.

47. The method according to claim 46, wherein said blood collector means comprises a blood collection bag containing an anticoagulant, so that step (b) further comprises the step of mixing the whole blood with said anticoagulant.

48. The method according to claim 46, further comprising, following step (d) and prior to step (e), the step of passing a physiologically isotonic solution through said filter means to complete filtration of the whole blood by said filter means.

49. The method according to claim 46, further comprising, following step (g), the step of adding a preservative for erythrocytes to the separated erythrocytes.

50. The method of claim 46, wherein the filtered blood contains less than 0.9% leukocytes.

51. A method for separating blood into blood components, comprising the steps of:
  (a) providing a blood component separator unit having a blood collector means fluid-tightly connected to filter means for removing leukocytes and platelets from whole blood, said filter means being fluid-tightly connected to a primary bag through sealable, cuttable conduit means, wherein said blood component separator unit is a substantially closed system that is only open to the outside where the blood collector means collects blood from a donor;
  (b) collecting, from a donor, whole blood comprising plasma, erythrocytes, leukocytes and platelets;
  (c) passing the whole blood through said filter means for removing leukocytes and platelets to produce a filtered blood containing the plasma and the erythrocytes;
  (d) discharging the filtered blood from said filter means into said primary bag through said conduit means;
  (e) sealing said conduit means at least at one portion intermediate to the ends thereof;
  (f) cutting said conduit means portion to separate said conduit means into a filter means-side unsealed or sealed conduit portion and a primary bag-side sealed conduit portion to thereby disconnect from said filter means said primary bag containing the filtered blood, said disconnected primary bag being sealed by virtue of said primary bag-side sealed conduit portion connected to said primary bag; and
  (g) centrifuging the filtered blood in said primary bag, wherein the filtered blood is separated into the erythrocytes and the plasma.

52. The method according to claim 51, wherein said blood collector means comprises a blood collection bag containing an anticoagulant, so that step (b) further comprises the step of mixing the whole blood with said anticoagulant.

53. The method according to claim 51, further comprising, following step (d) and prior to step (e), the step of passing a physiologically isotonic solution through said filter means to complete filtration of the whole blood by said filter means.

54. The method according to claim 51, further comprising, following step (g), the step of adding a preservative for erythrocytes to the separated erythrocytes.

55. A method for aseptically separating blood into blood components, comprising the steps of:
  (a) providing blood collector means fluid-tightly connected to filter means for removing leukocytes and platelets from whole blood, said filter means being fluid-tightly connected to a primary bag through sealable, cuttable conduit means;
  (b) collecting, from a donor, whole blood comprising plasma, erythrocytes, leukocytes and platelets;
  (c) passing the whole blood through said filter means for removing leukocytes and platelets to produce a filtered blood containing the plasma and the erythrocytes;
  (d) discharging the filtered blood from said filter means into said primary bag through said conduit means;
  (e) sealing said conduit means at least at one portion intermediate to the ends thereof;
  (f) cutting said conduit means portion to separate said conduit means into a filter means-side unsealed or sealed conduit portion and a primary bag-side sealed conduit portion to thereby disconnect from said filter means said primary bag containing the filtered blood, said disconnected primary bag being sealed by virture of said primary bag-side sealed conduit portion connected to said primary bag; and
  (g) centrifuging the filtered blood in said primary bag, wherein the filtered blood is separated into the erythrocytes and the plasma and blood components are separated aseptically.

56. The method according to claim 55, wherein said blood collector means comprises a blood collection bag containing an anticoagulant, so that step (*b*) further comprises the step of mixing the whole blood with said anticoagulant.

57. The method according to claim 55, further comprising, following step (*d*) and prior to step (*e*), the step of passing a physiologically isotonic solution through said filter means to complete filtration of the whole blood by said filter means.

58. The method according to claim 55, further comprising, following step (*g*), the step of adding a preservative for erythrocytes to the separated erythrocytes.

59. A method for separating blood into blood components, comprising the steps of:

(*a*) providing blood collector means fluid-tightly connected to filter means for removing leukocytes and platelets from whole blood, said filter means being fluid-tightly connected to a primary bag through sealable, cuttable conduit means, said primary bag being connected to a satellite bag system having at least one satellite bag through sealable, cuttable conduit means;

(*b*) collecting, from a donor, whole blood comprising plasma, erythrocytes, leukocytes and platelets;

(*c*) passing the whole blood through said filter means for removing leukocytes and platelets to produce a filtered blood containing the plasma and the erythrocytes;

(*d*) discharging the filtered blood from said filter means into said primary bag through said conduit means;

(*e*) sealing said conduit means at least at one portion intermediate to the ends thereof;

(*f*) cutting said conduit means portion to separate said conduit means into a filter means-side unsealed or sealed conduit portion and a primary bag-side sealed conduit portion to thereby disconnect from said filter means said primary bag containing the filtered blood, said disconnected primary bag being sealed by virtue of said primary bag-side sealed conduit portion connected to said primary bag;

(*g*) centrifuging the filtered blood in said primary bag, wherein the filtered blood is separated into the erythrocytes and the plasma; and (*h*) transferring one or more blood components to said satellite bag system to obtain, separately from each other, plasma and erythrocytes, whereby plasma suitable for transfusion and erythrocytes suitable for transfusion are obtained.

60. The method according to claim 59, wherein said blood collector means comprises a blood collection bag containing an anticoagulant, so that step (*b*) further comprises the step of mixing the whole blood with said anticoagulant.

61. The method according to claim 59, further comprising, following step (*d*) and prior to step (*e*), the step of passing a physiologically isotonic solution through said filter means to complete filtration of the whole blood by said filter means.

62. The method according to claim 59, further comprising, following step (*h*), the step of adding a preservative for erythrocytes to the separated erythrocytes.

\* \* \* \* \*